US006492146B1

(12) United States Patent
De Ferra et al.

(10) Patent No.: US 6,492,146 B1
(45) Date of Patent: Dec. 10, 2002

(54) PROCESS FOR THE PREPARATION OF PHOSPHATIDYLSERINES

(75) Inventors: Lorenzo De Ferra, Patrica (IT); Pietro Massardo, Patrica (IT)

(73) Assignee: Chemi S.p.A., Patrica (IT)

( * ) Notice: Subject to any disclaimer, the term of this patent is extended or adjusted under 35 U.S.C. 154(b) by 0 days.

(21) Appl. No.: 09/550,819

(22) Filed: Apr. 18, 2000

(30) Foreign Application Priority Data

Apr. 28, 1999 (IT) .......................................... MI99A0895

(51) Int. Cl.[7] .................................................. C12P 7/64
(52) U.S. Cl. ............................ 435/134; 584/82; 584/78
(58) Field of Search ............................ 554/19, 78, 82; 435/106, 116, 253.5, 886, 134

(56) References Cited

U.S. PATENT DOCUMENTS 4,845,028 A * 7/1989 Imamura et al. ............... 435/15
5,700,668 A * 12/1997 De Ferra et al. ............. 435/106

FOREIGN PATENT DOCUMENTS

| EP | 0776976 | 6/1997 |
| EP | 0819760 | 1/1998 |
| WO | 87/00173 | * 1/1987 |

OTHER PUBLICATIONS

Tomlinson et al, Extracts from fermentation residue and their use as improvers for yeast-raised goods, AN 1988:548265 CAPLUS, 1988.*

Comfurius et al., Journal of Lipid Research, vol. 31, pp. 1719–1721, 1990.*

Confurius et al., "Enzymatic synthesis of phosphatidylserine on small scale by use of a one–phase system", Journal of Lipid Research, vol. 31, pp. 1719–1721, 1990.*

Juneja L R et al: Conversion of Phosphatidylcholine to Phosphatidylserine by Various Phospholipases D in the Presence of L– or D–Serine—Biochimica et Biophysica Acta,NL,Amsterdam, vol. 1003, No. 3, 1989, pp. 277–283, XP000603423– ISSN:0006–3002 * The Whole Document*.

Confurius, P. et al: Enzymatic Synthesis of Phosphatidylserine on Small Scale by Use of a One–Phase System— Journal of Lipid Research, vol. 31, 1990, pp. 1719–1721, XP002145532 * The Whole Document *.

Confurius P et al: "The Enzymatic Synthesis of Phosphatidylserine and Purification by CM–Cellulose Column Chromatography" Biochimica et Biophysica Acta, NL, Amsterdam, vol. 488, No. 1, Jul. 20, 1977, pp. 36–42, XP000603420 ISSN: 0006–3002 * p. 37, Paragraph 2—Paragraph 5 *.

* cited by examiner

*Primary Examiner*—Deborah D. Carr
(74) *Attorney, Agent, or Firm*—Bucknam & Archer

(57) ABSTRACT

A process for the preparation of phosphatidylserines, comprising the reaction of phosphatides, such as phosphatidylcholine and phosphatidylethanolamine, with racemic or enantiomerically pure Serine, preferably with (L)-Serine, wherein said reaction is carried out in an aqueous dispersion of said phosphatides in the presence of a phospholipase D (PLD) and of calcium salts.

14 Claims, No Drawings

PROCESS FOR THE PREPARATION OF PHOSPHATIDYLSERINES

FIELD OF THE INVENTION

The present invention relates to a process for the preparation of phosphatidylserines.

More particularly, the invention relates to a process for the preparation of phosphatidylserines starting from natural or synthetic phospholipids, by reacting them with Serine in an aqueous medium.

BACKGROUND OF THE PRIOR ART

Phosphatidylserines have manifold importance, in particular in the production of pharmaceutical compositions suitable for the therapy of cerebral involutive disorders of different nature, such as senile decline or vascular pathologies, in the preparation of particular liposome formulations, and, more recently, the commercialisation of dietetic compositions containing natural lecithins, in particular soy lecithin, enriched in phosphatidyl-(L)-Serine, hereinafter referred to as PS, also containing polyunsaturated fatty acid acyl residues.

As industrial amounts of low-cost PS are increasingly needed, applicants carried out an extensive study in order to find conditions for the preparation of this product fulfilling the requirements of practicability on an industrial scale.

U.S. Pat. No. 5,700,668, in, discloses a process for the preparation of PS, which, contrary to those of the prior art (see, in particular, Comfurius P et al., Biochim. Biophys. Acta 488, 36 (1977); Yamane et al., Biochim. Biophys. Acta 1003, 277 (1989); JP-A-63 036,791; JP-A-02 079,990 and J.Chem.Soc. Perkin Trans. 1, 919 (1995)) allows to prepare PS in good yields on an industrial scale also from unpurified starting materials and without need for chromatographic purifications.

The process disclosed in said Patent comprises the reaction of natural or synthetic phosphatides with Serine in a diphasic system consisting of a solution of the starting phosphatide in an organic solvent, typically toluene, and of an aqueous solution containing Serine and phospholipase D. Keeping said system thoroughly stirred, phosphatides are transformed into PS which can be recovered from the organic phase by precipitation with acetone.

A similar process, although providing phosphatidylserine on large scale in good yields, deviates from the present trend for industrial chemical processes involving reduced use of organic solvents and minimizing by-products. This process, in fact, involves the use (and the recycle) of remarkable amounts of organic solvents and their recovery both during the reaction and during the isolation of the end product.

SUMMARY OF THE INVENTION

The present invention aims at providing a process for the preparation of phosphatidylserines on an industrial scale, which overcomes the drawbacks mentioned above with reference to the prior art.

This problem has been solved, according to the invention, by a process for the preparation of phosphatidylserines of formula (I)

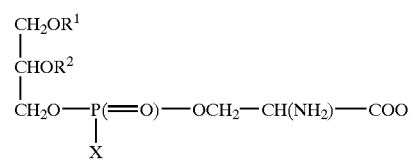

in which $R_1$ and $R_2$ are independently saturated, monounsaturated or polyunsaturated acyl $C_{10}$–$C_{30}$, X=OH or OM, wherein M=alkali or alkaline-earth metal, ammonium, alkylammonium (including the inner salt), comprising the reaction of phosphatides of general formula (II)

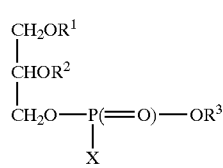

in which $R_1$, $R_2$ and X have the meanings defined above and $R_3$=$CH_2$—$CH_2$—$NH_2$ or $CH_2$—$CH_2$—$N^{3\oplus}(CH_3)_3$, with racemic or enantiomerically pure Serine, preferably with (L)-Serine, in the presence of a phospholipase D (PLD), characterized in that the reaction is carried out in an aqueous dispersion preferably in the presence of calcium salts. Serine is usually added to a buffered aqueous dispersions of phosphatides.

The starting material used in the process can be either a synthetic phosphatidylcholine (PC) such as DiMyristoylPhosphatidylCholine (DMPC), or a natural phosphatidylcholine or a mixture of phospholipids such as soy or egg lecithin or one of the commercially available phospholipid mixtures obtained by partial purification of soy or egg lecithin.

As far as the cost of the process is concerned, it is particularly convenient to use starting materials derived from lecithin in view of both their lower cost and the fact that phosphatidylethanolamine (PE), which is an important component of these mixtures, is transformed into PS under these reaction conditions.

The starting material should be thoroughly dispersed in an aqueous medium before the addition of the other reagents, in order to promote reactivity.

The dispersion is carried out keeping the starting phospholipide material under stirring for 1–10 hours at 20–50° C. with 3–10 volumes of water or saline solutions.

The use of surfactants in this step promotes the dispersion of the substrate and therefore the reaction rate.

Ionic or non-ionic surfactants can be conveniently used, more conveniently the surfactant is bis(2-ethylhexyl) sulfosuccinate sodium salt (AOT) or Tween 80[(R)] in amounts from 0.01 to 0.4 g per gram of substrate.

The effect of these surfactants is particularly favourable when using phosphatidylcholines, such as DMPC, which have poor tendency to disperse in aqueous medium.

A further feature of this invention is that it is possible to easily remove the alcohol solvents, and in particular ethanol, which often contaminates the preparations of natural phospholipids (for example Phosphatidylcholine-enriched fractions obtained from soy lecithin) and which interfere in the subsequent reaction of formation of PS as they react in the presence of phospholipase D to give the corresponding phosphatidyl derivatives (such as phosphatidylethanol when ethanol is present in the mixture).

This removal can be conveniently carried out by dispersing the starting phospholipid in an aqueous saline solution, decanting the suspension and removing the liquid phase which contains ethanol dissolved therein.

As aqueous saline solution can be used any saline solution having sufficiently high density to easily separate the starting material, preferably a solution of calcium chloride or of Sodium Acetate/Acetic acid buffer or of both of them.

The starting material aqueous dispersion is added with an aqueous solution containing Serine, Calcium Chloride, a uffer to control pH and phospholipase D.

The amount of Serine will conveniently range from 4 to 20 mols of Serine per mol of phospholipid to be converted nto PS. Serine can be in the D, L or racemic forms to obtain in any case the corresponding phosphatidyl derivatives.

Calcium chloride is the source of calcium ion which favours the Phospholipase D-catalysed reactions; furthermore, the presence of calcium ion induces the separation of Phosphatidylserine in an easily filterable form after completion of the reaction.

The concentration of calcium chloride preferably ranges from 0.05 to 0.5 M.

The pH of the aqueous solution will depend on the origin of the used enzyme and it will preferably range from pH=4 to pH=9 included. In case of enzymes exerting their activity in substantially acid medium, the aqueous solution will be preferably buffered with 0.02M to 0.2M acetate buffer.

An enzyme having a transphosphatidylating activity higher than the hydrolysing activity should conveniently be used as the enzyme for carrying out the reaction; an enzyme of fermentative origin may be advantageously used, more conveniently the enzyme obtained by fermentation of the microorganism deposited at the ATCC under the number 55717.

The enzyme can be used either in the crude form, namely the fermentation mixture after filtering off the microorganism, or, more preferably, after purification by ultrafiltration through membrane with suitable cut-off to remove low molecular weight impurities. The enzyme-rich solution from the ultrafiltration can be used as it is or it can be freeze-dried to obtain the enzyme in the solid form; the enzyme amount preferably ranges from 10 to 100 units per gram of phosphatide (the enzymatic activity is determined with the test described in Biotechn Techn 7 795 (1993)).

The reaction is preferably carried out at 25–60° C., most preferably from 40 to 50° C.

PS is recovered by filtration of the reaction mixture, washing the solid with water to remove Serine and the present salts.

A particularly advantageous aspect of the process according to the invention is that the reaction product (PS) is separated from the reaction mixture in such a form that the recovery can be effected by simple filtration without need for precipitations by addition of solvents.

The main advantage of the process according to the invention is the possibility, unexpected in view of the prior art, to carry out the transphosphatidylation reaction of phosphatidylcholine and of similar phosphatides in an aqueous medium, to obtain phosphatidylserine of good purity and in highly satisfactory yields.

The features and the advantages of the process of the invention will be further disclosed by the following examples.

EXAMPLE 1

5 g of 95% purity Soy phosphatidylcholine were added to 30 ml of 1.0M acetate buffer pH 4.5. The mixture was stirred at 40° C. for 1 hour, to homogeneously disperse the phospholipid in the aqueous phase. The enzymatic solution consisted of 80 ml of a phospholipase D solution of 2 U/g activity, obtained by fermentation of the microorganism deposited under the number ATCC55717, then dialysing the crude enzyme solution through an ultrafiltration membrane with cutoff 10,000 Daltons until complete removal of the low molecular weight impurities, were used as the enzyme. This enzyme solution was added to added 40 g of L-Serine, 2.9 g of Calcium Chloride. The resulting solution was added to the Phosphatidylcholine dispersion and the mixture was heated to 45° C.

The mixture was stirred for 6 hours. The solid was filtered, washed with water and dried. Final weight 4.24 g.

HPLC Composition: PS 90.7%, PC 1.4%, PA (phosphatidic acid) 6.2%.

EXAMPLE 2

5 g of 95% purity Soy phosphatidylcholine were added to 30 ml of 0.1M acetate buffer pH 4.5 containing 0.08 g of Tween 80$^{(R)}$. The mixture was stirred at 40° C. for 1 hour, to homogeneously disperse the phospholipid in the aqueous phase. 80 ml of a Phospholipase D solution of 2 U/g activity, obtained as described in example 1, were added to 40 g of L-Serine, 2.9 g of Calcium Chloride. The resulting solution was added to the Phosphatidylcholine dispersion and the mixture was heated to 45° C. After 90 minutes, HPLC analysis showed the composition: PS 69.7% PC 11.6% PA 5.3%.

The mixture was stirred for a further 4 hours. The solid was filtered, washed with water and dried. Final weight 4.76 g.

HPLC composition: PS 90.2%, PC 0.6%, PA 6.4%.

EXAMPLE 3

5 g of 95% purity Soy phosphatidylcholine were added to 30 ml of 0.1M acetate buffer of pH 4.5 containing 0.3 g of AOT. The mixture was stirred at 40° C. for 1 hour, to homogeneously disperse the phospholipid in the aqueous phase. 80 ml of a Phospholipase D solution of 2 U/ng activity, obtained as described in example 1, were added with 40 g of L-Serine, 2.9 g of Calcium Chloride. The resulting solution was added to the Phosphatidylcholine dispersion and the mixture was heated to 45° C.

After reacting for 6 hours, the solid was filtered, washed with water and dried. Final weight 4.16 g.

HPLC composition: PS 88.8%, PC 0.6%, PA 4.1%.

EXAMPLE 4

25 g of a phospholipid mixture obtained by enriching soy lecithin whose main components are PC 66% PE 17% PA 2% were added to 100 ml of 0.1M acetate buffer pH 4.5. The mixture was stirred at 40° C. for 1 hour, to homogeneously disperse the phospholipid in the aqueous phase. A solution of 80 ml 0.1M acetate buffer pH 4.5, 40 g of L-Serine, 2.9 g of Calcium Chloride was prepared separately; this solution was added to 188 mg of the solid resulting from freeze-drying the Phospholipase D solution obtained as described in example 1; the activity of this solid is 0.9 U/mg. The resulting solution was added to the Phospholipid dispersion and the mixture was heated to 45° C.

The mixture was stirred for 3 hours. The solid was filtered, washed with water and dried. Final weight 22.8 g.

HPLC composition: PS 59.8%, PC 1.6%, PA 6.1%, PE 6.7%.

EXAMPLE 5

25 g of the Phospholipid mixture used as starting material in example 4 were added to 100 ml of 0.1M acetate buffer of pH 4.5. The mixture was stirred at 40° C. for 1 hour, to homogeneously disperse the phospholipid in the aqueous phase. A solution of 80 ml 0.1M acetate buffer pH 4.5, 10 g of L-Serine, 2.9 g of Calcium Chloride was prepared separately; this solution was added to 90 mg of the freeze-dried enzyme prepared as described in example 4. The resulting solution was added to the Phospholipid dispersion and the mixture was heated to 45° C. and stirred for 16 hours. The final composition was determined by HPLC: PS 39.1%, PC 8.3%, PA 16.6%, PE 6.8%.

EXAMPLE 6

The reaction was carried out in the same conditions as described in example 5, but keeping a temperature of 55° C. during the reaction. After 16 hours the reaction was interrupted. HPLC analysis showed the following composition: PS 41.7%, PC 8.3%, PA 11.0%, PE 9.9%.

EXAMPLE 7

The reaction was carried out in the same conditions as described in example 4, but without the addition of Calcium chloride. After 20 hours the reaction was interrupted. HPLC analysis showed the following composition: PS 41.2%, PC 15.9%, PA 10.9%, PE 7.4%.

EXAMPLE 8

2 g of the phospholipids mixture used as starting material in example 4 were added to a solution of 3 g of Calcium Chloride in 40 ml Water in a separatory funnel; the mixture was stirred at 25° C. for 1 hour; stirring was interrupted and, after three hour standing, 36 ml of aqueous phase were drawn off the bottom valve. A solution of 6.5 ml 0.1M acetate buffer pH 4.5, 3.2 g of L-Serine was prepared separately; this solution was added to 15 mg of the freeze-dried enzyme prepared as described in example 4. The resulting solution was added to the Phospholipids dispersion and the mixture was heated to 45° C.

The reaction was stirred for 1 hour. The final composition was determined by HPLC: PS 55.7%, PC 9.4%, PA 4.0%, PE 9.0%. The formation of Phosphatidylethanol in this reaction was below the TLC detectability limit (0.1%)

EXAMPLE 9

5 g of DiMyristoylPhosphatidylcholine (DMPC), 1.6 g of Tween 80$^{(R)}$ and 30 ml 0.1M sodium acetate buffer pH 4.5 were stirred at 45° C. for 1 hour. The dispersion was added to a solution of 80 ml of aqueous Phospholipase D solution obtained as described in example 1, 40 g of L-Serine and 2.9 g of Calcium Chloride, the temperature was brought to 50° C. keeping stirring for 17 hours. The solid was filtered, washed with water and dried. Final weight 5.4 g.

HPLC composition: PS 83.2%, PC 4.3%, PA 11.7%.

EXAMPLE 9

5 g of DiMyristoylPhosphatidylcholine (DMPC), 1.0 g of AOT and 30 ml of 0.1M sodium acetate buffer pH 4.5 were stirred at 50° C. for 45 minutes. The dispersion was added to a solution of 80 ml of aqueous Phospholipase D solution obtained as described in example 1, 40 g of L-Serine and 2.9 g of Calcium Chloride, the temperature was brought to 50° C. keeping stirring for 20 hours. The solid was filtered, washed with water and dried. Final weight 3.66 g.

HPLC composition: PS 85.2%, PC 10.5%, PA 3.5%.

EXAMPLE 11

10 g of a non-deoleated soy lecithin fraction enriched in PC (composition: Triglycerids 50%, PC 35%, PE 8%) were added to 30 ml of sodium acetate buffer pH 4.5 and left under stirring at 25° C. for 1 hour. The mixture was added to a solution of 80 ml of solution of the phospholipase D enzyme prepared as described in example 1, 40 g of L-Serine and 2.9 g of Calcium chloride. The reaction mixture was stirred at 45° C. for 11 hours, the aqueous phase was separated and the gummy solid was added to 100 ml acetone. After filtration and drying, 3.9 g of the product were obtained. HPLC analysis: PS 58%, PC 2.0%, PA 17.0, PE 1.8%.

What is claimed is:

1. A process for the preparation of phosphatidyl-serine of formula (I)

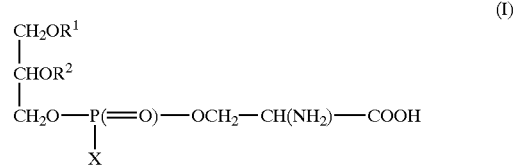

(I)

In which $R^1$ and $R^2$ are independently saturated, monounsaturated or polyunsaturated acyl $C_{10}$–$C_{30}$, X=OH or OM, wherein M is an inner salt, alkali or alkaline-earth metal, ammonium or alkylammonium comprising the reaction of a phosphatide of general formula (II)

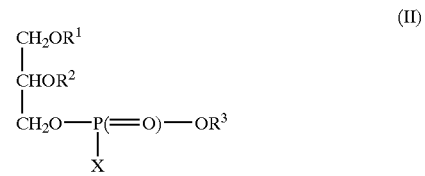

(II)

In which $R^1$, $R^2$ and X have the meanings defined above and $R^3$—$CH_2$—$CH_2$—$NH_2$ or $CH_2$—$CH_2$—$N^+(CH_3)_3$, with racemic or enantiomerically pure serine, or (L)-serine, in the presence of the enzyme phospholipase D (PLD) and a surfactant in a quantity not greater than 0.4 grams per gram of substrate, wherein the reaction medium is an aqueous dispersion free of organic solvents.

2. The process as claimed in claim 1, wherein the reaction is carried out in the presence of a calcium salt.

3. The process as claimed in claim 2, wherein said calcium salt is calcium chloride present in a concentration ranging between 0.05 and 0.5 M.

4. The process as claimed in claim 1, wherein the amount of serine ranges from 4 to 20 moles per mole of phosphatides.

5. The process as claimed in claim 1, wherein said phosphatide, before being subjected to the reaction with serine, is purified by removing alcohols by suspending said phosphatide in an aqueous saline solution and subsequently decanting the liquid phase which contains the alcohols.

6. The process as claimed in claim 5, wherein said aqueous saline solution is a member selected from the group consisting of calcium chloride, an acetic acid/sodium acetate buffer solution and calcium chloride with an acetic acid/sodium acetate solution.

7. The process as claimed in claim 1, wherein said reaction is carried out at a temperature ranging between 25 and 60° C.

8. The process according to claim 1, wherein said phospholipase D is obtained from centrifuged fermentation broths of micro-organisms strains producing extracellular PLD with high transphosphatidylation capability.

9. The process as claimed in claim 8, wherein said phospholipase D is produced by Streptomyces ATCC 55717 strain.

10. The process according to claim 1, wherein the aqueous dispersion of said substrate is obtained by mixing said phosphatide with 3–10 volumes of water or of a saline solution and keeping the resulting mixture under stirring for 1–10 hours at 20–50° C.

11. The process as claimed in claim 1, wherein phosphatidylserine of formula (I) is recovered from the reaction mixture by filtration and washing with water.

12. The process as claimed in claim 1, wherein said phosphatide is a mixture of phosphatidylcholine and phosphatidylethanolamine of natural origin selected from soy and egg lecithins with a phospholipid content ranging from 20 to 95%.

13. The process as claimed in claim 7, wherein said phosphatide of formula (II) is a synthetic phosphatidylcholine.

14. The process according to claim 1, wherein said surfactant is bis(2-ethylhexyl) sulfosuccinate sodium salt (AOT) or Tween R80(R).

* * * * *